(12) United States Patent
Himmelsbach et al.

(10) Patent No.: US 7,196,091 B2
(45) Date of Patent: Mar. 27, 2007

(54) BICYCLIC HETEROCYCLES, PHARMACEUTICAL COMPOSITIONS CONTAINING THESE COMPOUNDS, THEIR USE AND PROCESSES FOR PREPARING THEM

(75) Inventors: Frank Himmelsbach, Mittelbiberach (DE); Rainer Soyka, Biberach (DE); Birgit Jung, Laupheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/860,453

(22) Filed: Jun. 3, 2004

(65) Prior Publication Data

US 2005/0014772 A1 Jan. 20, 2005

Related U.S. Application Data

(60) Provisional application No. 60/480,720, filed on Jun. 23, 2003.

(30) Foreign Application Priority Data

Jun. 6, 2003 (DE) ................. 103 26 186

(51) Int. Cl.
A61K 31/517 (2006.01)
C07D 239/78 (2006.01)
(52) U.S. Cl. ..................... 514/258; 544/253
(58) Field of Classification Search ............... 544/253; 514/258
See application file for complete search history.

(56) References Cited

U.S. PATENT DOCUMENTS 5,770,599 A 6/1998 Gibson
2002/0082271 A1 6/2002 Himmelsbach

FOREIGN PATENT DOCUMENTS

WO WO 96/33980 10/1996
WO WO 00/55141 9/2000
WO WO2001077085 * 10/2001
WO WO 02/18351 3/2002

OTHER PUBLICATIONS

Barker, A. J., et al. "Studies leading to the identification of ZD1839 (iressa): an orally active, selective epidermal growth factor receptor tyrosine kinase inhibitor targeted to the treatment of cancer" Bioorganic & Medicinal Chem. Letters 11(14), 2001, pp. 1911-1914.
Kashima, Choji, et al. "Synthesis and Reaction of Optically Active Morpholinones" J. Chem. Soc. Perkin Trans. 1, 1988, pp. 1521-1526.
Gore, Jeff, et al. "The Structure of a Human Metabolite of Pholcodine" Aust. J. Chem. 49, 11, 1996, pp. 1235-1242.

* cited by examiner

*Primary Examiner*—Rita Desai
(74) *Attorney, Agent, or Firm*—Michael P. Morris; Mary-Ellen M. Devlin; David Dow

(57) ABSTRACT

The present invention relates to bicyclic heterocycles of general formula

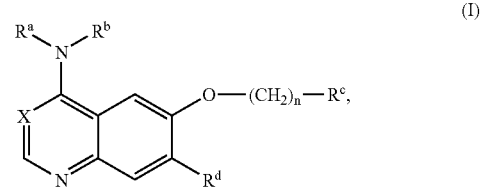

(I)

wherein
$R^a$, $R^b$, $R^c$, $R^d$, X and n are defined as in claim 1, the tautomers, the stereoisomers, the mixtures thereof and the salts thereof, particularly the physiologically acceptable salts thereof with inorganic or organic acids which have valuable pharmacological properties, particularly an inhibiting effect on the signal transduction mediated by tyrosine kinases, their use in treating diseases, particularly tumoral diseases, as well as benign prostatic hyperplasia (BPH), diseases of the lungs and respiratory tract and the preparation thereof.

6 Claims, No Drawings

BICYCLIC HETEROCYCLES, PHARMACEUTICAL COMPOSITIONS CONTAINING THESE COMPOUNDS, THEIR USE AND PROCESSES FOR PREPARING THEM

This application claims benefit of U.S. Ser. No. 60/480,720, dated Jun. 23, 2003, and claims priority to Federal Republic of Germany Application No. DE 103 26 186.9, dated Jun. 6, 2003, each of which is incorporated by reference in its entirety.

The present invention relates to bicyclic heterocycles of general formula

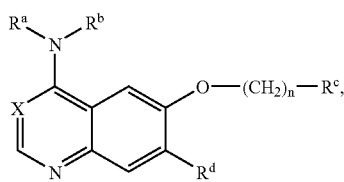

(I)

the tautomers, the stereoisomers, the mixtures thereof and the salts thereof, particularly the physiologically acceptable salts thereof with inorganic or organic acids which have valuable pharmacological properties, particularly an inhibiting effect on the signal transduction mediated by tyrosine kinases, their use in treating diseases, particularly tumoral diseases, as well as benign prostatic hyperplasia (BPH), diseases of the lungs and respiratory tract and the preparation thereof.

In the above general formula I $R^a$ denotes a hydrogen atom or a $C_{1-3}$-alkyl group, $R^b$ denotes a phenyl or 1-phenylethyl group, wherein the phenyl nucleus is substituted in each case by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, a phenyloxy or phenylmethoxy group, while the phenyl moiety of the above-mentioned groups is optionally substituted by a fluorine or chlorine atom, or a pyridyloxy or pyridinylmethoxy group, while the pyridinyl moiety of the above-mentioned groups is optionally substituted by a methyl or trifluoromethyl group, a methyl or methoxy group substituted by 1 to 3 fluorine atoms or a cyano, nitro or amino group, and $R^3$ denotes a hydrogen, fluorine, chlorine or bromine atom or a methyl or trifluoromethyl group, $R^c$ denotes a (2-hydroxyethyl)amino group wherein the carbon skeleton of the (2-hydroxyethyl)-moiety is optionally substituted by one or two $C_{1-3}$-alkyl groups, an N-(2-hydroxyethyl)-N-($C_{1-3}$-alkyl)-amino group wherein the carbon skeleton of the (2-hydroxyethyl)-moiety is optionally substituted by one or two $C_{1-3}$-alkyl groups, or a 2-oxo-oxazolidin-3-yl group optionally substituted by one or two $C_{1-3}$-alkyl groups, $R^d$ denotes a hydrogen atom, a hydroxy group, a $C_{1-3}$-alkyloxy group, a $C_{2-4}$-alkyloxy group which is substituted by a group $R^4$, while $R^4$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo-[3.2.1]oct-3-yl, piperazin-1-yl, 4-$C_{1-3}$-alkyl-piperazin-1-yl, homopiperazin-1-yl or 4-$C_{1-3}$-alkyl-homopiperazin-1-yl group, while the above-mentioned pyrrolidinyl, piperidinyl, piperazinyl and morpholinyl groups may each be substituted by one or two $C_{1-3}$-alkyl groups, a $C_{3-7}$-cycloalkyloxy or $C_{3-7}$-cycloalkyl-$C_{1-3}$-alkyloxy group, a tetrahydrofuran-3-yloxy, tetrahydropyran-3-yloxy or tetrahydropyran-4-yloxy group, or a tetrahydrofuranyl-$C_{1-3}$-alkyloxy or tetrahydropyranyl-$C_{1-3}$-alkyloxy group, X denotes a methyne group substituted by a cyano group or a nitrogen atom and n denotes the number 2, 3 or 4, while, unless otherwise stated, the above-mentioned alkyl groups may be straight-chain or branched, the tautomers, their stereoisomers, the mixtures thereof and the salts thereof.

Preferred compounds of the above general formula I are those wherein $R^a$ denotes a hydrogen atom, $R^b$ denotes a 3-bromophenyl, 3,4-difluorophenyl, 3-chloro-4-fluoro-phenyl or a 3-ethynylphenyl group, $R^c$ denotes a (2-hydroxypropyl)amino or N-(2-hydroxypropyl)-N—($C_{1-3}$-alkyl)-amino group, an N-(2-hydroxybutyl)amino or N-(2-hydroxybutyl)-N—($C_{1-3}$-alkyl)-amino group, a (2-hydroxy-2-methyl-propyl)amino or N-(2-hydroxy-2-methyl-propyl)-N—($C_{1-3}$-alkyl)-amino group, an N-(2-hydroxy-2-ethyl-butyl)amino or N-(2-hydroxy-2-ethyl-butyl)-N—($C_{1-3}$-alkyl)-amino group, or a 2-oxo-5-methyl-oxazolidin-3-yl, 2-oxo-5-ethyl-oxazolidin-3-yl, 2-oxo-5,5-dimethyl-oxazolidin-3-yl or 2-oxo-5,5-diethyl-oxazolidin-3-yl group, $R^d$ denotes a hydrogen atom, a methoxy, ethyloxy or 2-methoxyethyloxy group, a cyclobutyloxy, cyclopentyloxy or cyclohexyloxy group, a cyclopropylmethoxy, cyclobutylmethoxy, cyclopentylmethoxy or cyclohexylmethoxy group, a tetrahydrofuran-3-yloxy, tetrahydropyran-3-yloxy or tetrahydropyran-4-yloxy group, or a tetrahydrofuranylmethoxy or tetrahydropyranylmethoxy group, X denotes a nitrogen atom, and n denotes the number 2 or 3, the tautomers, their stereoisomers, the mixtures thereof and the salts thereof.

Particularly preferred compounds of the above general formula I are those wherein $R^a$ denotes a hydrogen atom, $R^b$ denotes a 3-chloro-4-fluoro-phenyl group or 3-ethynylphenyl group, $R^c$ denotes a (2-hydroxypropyl)amino group, an N-(2-hydroxypropyl)-N-methyl-amino or N-(2-hydroxypropyl)-N-ethyl-amino group, a (2-hydroxy-2-methyl-propyl)amino group, an N-(2-hydroxy-2-methyl-propyl)-N-methyl-amino or N-(2-hydroxy-2-methyl-propyl)-N-ethyl-amino group, or a 2-oxo-5-methyl-oxazolidin-3-yl or 2-oxo-5,5-dimethyl-oxazolidin-3-yl group, $R^d$ denotes a methoxy, ethyloxy or 2-methoxyethyloxy group, X denotes a nitrogen atom, and n denotes the number 2, the tautomers, the stereoisomers, the mixtures thereof and the salts thereof.

The following particularly preferred compounds of general formula I are now mentioned by way of example:
(a) (S)-4-[(3-chloro-4-fluoro-phenyl)amino]-6-[2-(2-oxo-5-methyl-oxazolidin-3-yl)ethyloxy]-7-methoxy-quinazoline
(b) (S)-4-[(3-chloro-4-fluoro-phenyl)amino]-6-{2-[(2-hydroxypropyl)amino]ethyloxy}-7-methoxy-quinazoline
(c) 4-[(3-chloro-4-fluoro-phenyl)amino]-6-{2-[(2-hydroxy-2-methyl-propyl)amino]ethyloxy}-7-methoxy-quinazoline
(d) 4-[(3-chloro-4-fluoro-phenyl)amino]-6-[2-(2-oxo-5,5-dimethyl-oxazolidin-3-yl)ethyloxy]-7-methoxy-quinazoline as well as the salts thereof.

The compounds of general formula I may be prepared by the following methods, for example:

a) reacting a compound of general formula

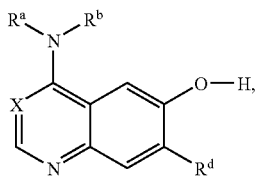

(II)

wherein $R^a$, $R^b$, $R^d$ and X are as hereinbefore defined, with a compound of general formula $Z^1$—(CH$_2$)$_n$—$R^c$ (III), wherein $R^c$ and n are as hereinbefore defined and $Z^1$ denotes a leaving group such as a halogen atom, e.g. a chlorine or bromine atom, a sulphonyloxy group such as a methanesulphonyloxy or p-toluenesulphonyloxy group or a hydroxy group. The reaction is conveniently carried out in a solvent such as ethanol, isopropanol, acetonitrile, toluene, tetrahydrofuran, dioxane, dimethylformamide, dimethylsulphoxide or N-methylpyrrolidinone, optionally in the presence of a base such as potassium carbonate or N-ethyl-diisopropylamine, at temperatures between 20° C. and 160° C. With a compound of general formula III wherein $Z^1$ denotes a hydroxy group, the reaction carried out is in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycol diethylether at temperatures between −50 and 150° C., but preferably at temperatures between −20 and 80° C.

b) In order to prepare compounds of general formula I wherein X denotes a nitrogen atom:

reacting a compound of general formula

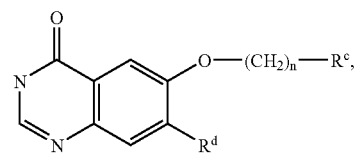

(IV)

wherein $R^c$, $R^d$ and n are as hereinbefore defined, with a halogenating agent, for example an acid halide such as thionyl chloride, thionyl bromide, phosphorus trichloride, phosphorus pentachloride or phosphorus oxychloride to obtain an intermediate compound of general formula (V),

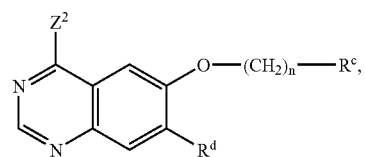

(V)

wherein $R^c$, $R^d$ and n are as hereinbefore defined and $Z^2$ denotes a halogen atom such as a chlorine or bromine atom, and subsequent reaction with a compound of general formula $R^a$—NH—$R^b$ (VI), wherein $R^a$ and $R^b$ are as hereinbefore defined.

The reaction with the halogenating agent is optionally carried out in a solvent such as methylene chloride, chloroform, acetonitrile or toluene and optionally in the presence of a base such as N,N-diethylaniline or N-ethyl-diisopropylamine at temperatures between 20° C. and 160° C. Preferably, however, the reaction is carried out with thionyl chloride and catalytic quantities of dimethylformamide at the boiling temperature of the reaction mixture.

The reaction of the compound of general formula (V) with a compound of general formula (VI) is conveniently carried out in a solvent such as ethanol, isopropanol, acetonitrile, dioxane or dimethylformamide, optionally in the presence of a base such as potassium carbonate or N-ethyl-diisopropylamine, at temperatures between 20° C. and 160° C.

c) reacting a compound of general formula

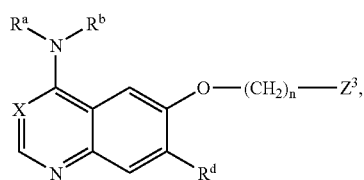

wherein $R^a$, $R^b$, $R^d$, X and n are as hereinbefore defined, and $Z^3$ denotes a leaving group such as a halogen atom, e.g. a chlorine or bromine atom, a sulphonyloxy group such as a methanesulphonyloxy or p-toluenesulphonyloxy group, with a compound of general formula

wherein $R^c$ is as hereinbefore defined.

The reaction is conveniently carried out in a solvent such as ethanol, isopropanol, acetonitrile, toluene, tetrahydrofuran, dioxane, dimethylformamide, dimethylsulphoxide or N-methylpyrrolidinone, optionally in the presence of a base such as potassium carbonate or N-ethyl-diisopropylamine, at temperatures between 20° C. and 160° C.

If according to the invention a compound of general formula I is obtained wherein $R^c$ denotes a 2-oxo-oxazolidin-3-yl group optionally substituted by one or two $C_{1-3}$-alkyl groups, this may be converted by hydrolysis, for example in the presence of an alkali metal hydroxide such as lithium hydroxide, sodium hydroxide or potassium hydroxide, into a compound wherein $R^c$ denotes a (2-hydroxyethyl)amino group, wherein the carbon skeleton of the (2-hydroxyethyl)-moiety is optionally substituted by one or two $C_{1-3}$-alkyl groups, and/or if a compound of general formula I is obtained wherein $R^c$ denotes a (2-hydroxyethyl)amino group, wherein the carbon skeleton of the (2-hydroxyethyl)-moiety is optionally substituted by one or two $C_{1-3}$-alkyl groups, this may be converted by reacting with a derivative of carbonic acid, for example phosgene, N,N'-carbonyldiimidazole or diphenyl carbonate, into a compound wherein $R^c$ denotes a 2-oxo-oxazolidin-3-yl group optionally substituted by one or two $C_{1-3}$-alkyl groups, and/or if a compound of general formula I is obtained which contains an amino, alkylamino or imino group this may be converted by alkylation or reductive alkylation, for example using formaldehyde or acetaldehyde and sodium triacetoxyborohydride, into a corresponding alkyl compound of general formula I.

Compounds of general formula I wherein $R^a$, $R^b$, $R^d$ and n are as hereinbefore defined, X denotes a nitrogen atom and $R^c$ denotes a (2-hydroxyethyl)amino group wherein the carbon skeleton of the (2-hydroxyethyl)-moiety is optionally substituted by one or two $C_{1-3}$-alkyl groups are suitable as starting compounds for preparing corresponding quinazoline derivatives of general formula

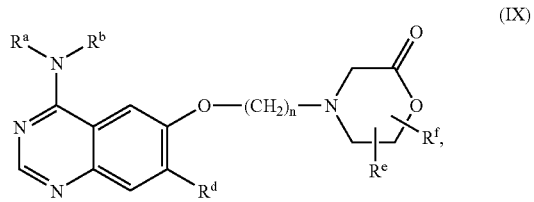

wherein $R^a$, $R^b$, $R^d$ and n are as hereinbefore defined and $R^e$ and $R^f$ independently of one another denote hydrogen atoms or $C_{1-3}$-alkyl groups. Compounds of this kind are described in WO 02/18351. The 2-oxomorpholine ring is synthesised by reacting the above-mentioned starting compounds with reactive acetic acid derivatives, for example with an α-haloacetate such as methyl α-bromoacetate.

The compounds of general formula (IX) are prepared by reacting the above-mentioned starting compounds, conveniently in a solvent such as acetonitrile, toluene, tetrahydrofuran, dioxane, dimethylformamide, dimethylsulphoxide or N-methylpyrrolidinone, optionally in the presence of a base such as potassium carbonate or N-ethyl-diisopropylamine, at temperatures between 20° C. and 160° C., preferably at temperatures between 0 and 50° C., and subsequently heating conveniently in a solvent such as toluene, dioxane, N-methylpyrrolidinone, methylethylketone, diethylketone or n-butyl acetate or mixtures thereof to 80–180° C., preferably 100–150° C.

In the reactions described hereinbefore, any reactive groups present such as hydroxy, amino, alkylamino or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be a formyl, acetyl, trifluoroacetyl, ethoxycarbonyl, tert butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II to VIII used as starting materials are known from the literature in some cases or may be obtained by methods known from the literature (cf. Examples I to XVI), optionally with additional inclusion of protecting groups. For example, the starting compounds for the compounds of general formula I according to the invention wherein X denotes a nitrogen atom and $R^c$ denotes a 2-oxo-oxazolidin-3-yl group optionally substituted by one or two $C_{1-3}$-alkyl groups may be obtained according to the following synthesis plan:

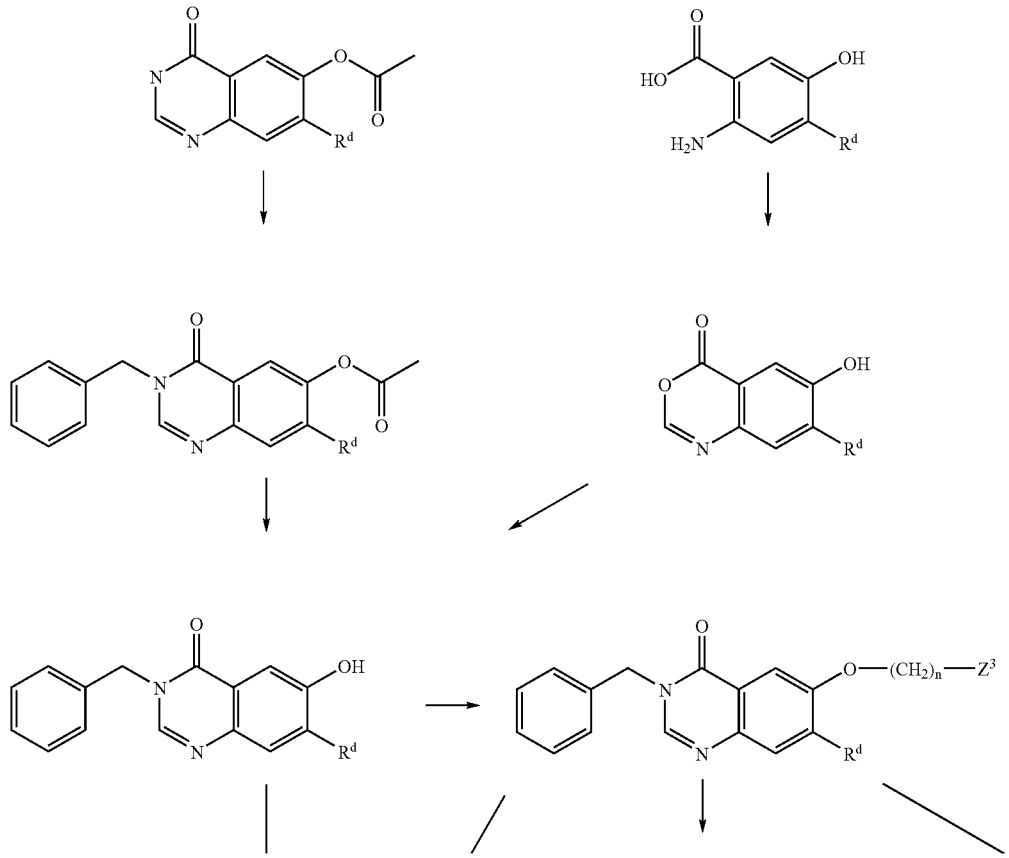

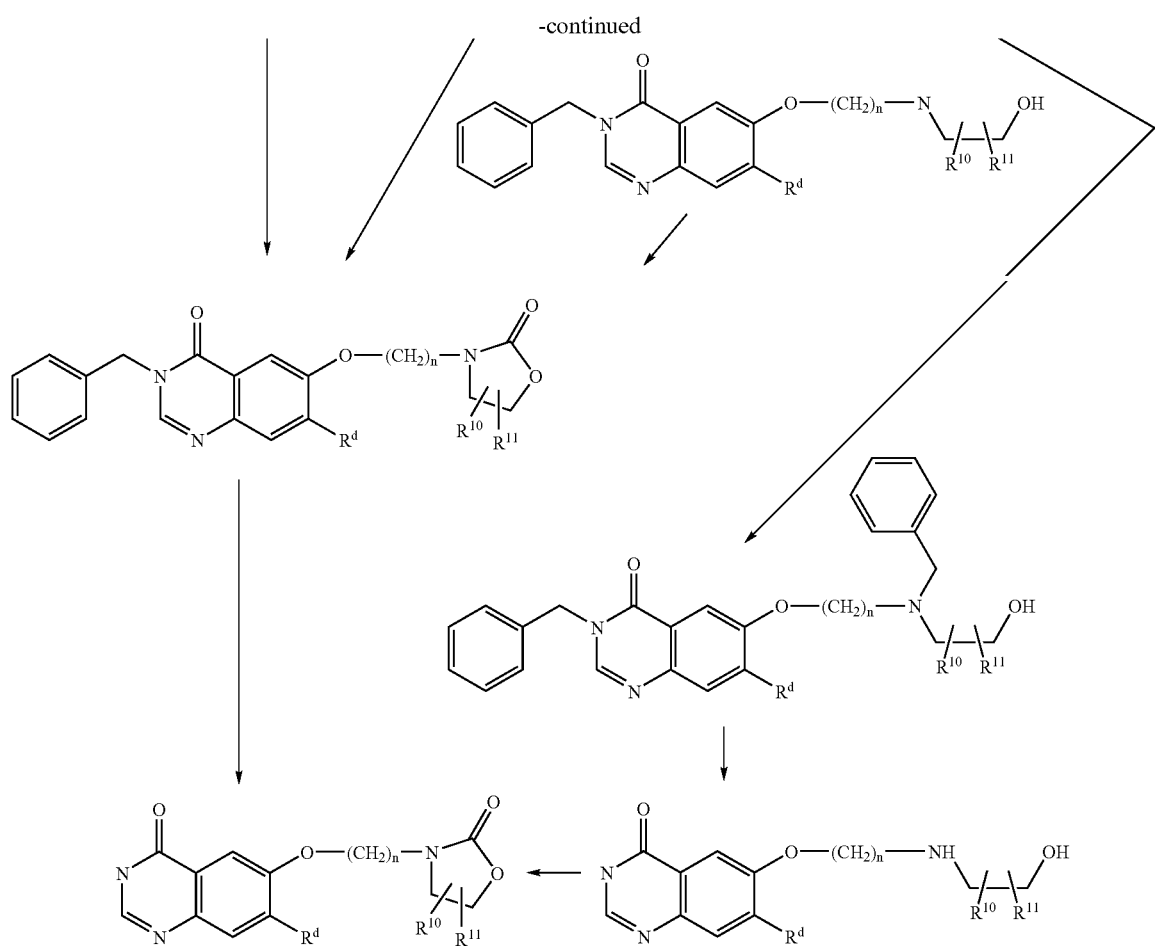

-continued where $R^d$ and $Z^3$ are as hereinbefore defined and $R^{10}$ and $R^{11}$, which may be identical or different, denote hydrogen atoms or $C_{1-3}$-alkyl groups. Instead of the benzyl group mentioned as a protective group in the 3 position of the 3,4-dihydro-4-oxo-quinazoline group it is also possible to use other protective groups such as the 4-methoxybenzyl, 2,4-dimethoxybenzyl, methoxymethyl, benzyloxymethyl, (2-methoxyethyl)oxymethyl, (2-trimethylsilylethyl)oxymethyl or the pivaloyloxymethyl group.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible to block the transmission of signals to components located further downstream.

The biological properties of the new compounds were investigated as follows:

The inhibition of human EGF-receptor kinase was determined using the cytoplasmatic tyrosine kinase domain (methionine 664 to alanine 1186, based on the sequence published in Nature 309 (1984), 418). To do this, the protein was expressed in Sf9 insect cells as a GST fusion protein using the Baculovirus expression system.

The enzyme activity was measured in the presence or absence of the test compounds in serial dilutions. The polymer pEY (4:1) produced by SIGMA was used as the substrate. Biotinylated pEY (bio-pEY) was added as the tracer substrate. Every 100 μl of reaction solution contained 10 μl of the inhibitor in 50% DMSO, 20 μl of the substrate solution (200 mM HEPES pH 7.4, 50 mM magnesium acetate, 2.5 mg/ml poly(EY), 5 μg/ml bio-pEY) and 20 μl of enzyme preparation. The enzyme reaction was started by the addition of 50 μl of a 100 μM ATP solution in 10 mM magnesium chloride. The dilution of the enzyme preparation was adjusted so that the incorporation of phosphate into the bio-pEY was linear in terms of time and quantity of enzyme. The enzyme preparation was diluted in 20 mM HEPES pH 7.4, 1 mM EDTA, 130 mM common salt, 0.05% Triton X-100, 1 mM DTT and 10% glycerol.

The enzyme assays were carried out at ambient temperature over a period of 30 minutes and were ended by the addition of 50 μl of a stopping solution (250 mM EDTA in 20 mM HEPES pH 7.4). 100 μl were placed on a streptavidin-coated microtitre plate and incubated for 60 minutes at ambient temperature. Then the plate was washed with 200 μl of a washing solution (50 mM Tris, 0.05% Tween 20). After the addition of 100 μl of a HRPO-labelled anti-PY antibody (PY20H Anti-PTyr:HRP produced by Transduction Laboratories, 250 ng/ml) it was incubated for 60 minutes. Then the microtitre plate was washed three times with 200 μl of washing solution. The samples were then combined with 100 μl of a TMB-peroxidase solution (A:B=1:1, Kirkegaard Perry Laboratories). After 10 minutes the reaction was stopped. The extinction was measured at $OD_{450\ nm}$ with an ELISA reader. All data points were measured three times.

The data were matched using an iterative calculation using an analytical programme for sigmoidal curves (Graph Pad Prism Version 3.0) with variable Hill pitch. All the iteration data released showed a correlation coefficient of more than 0.9 and the upper and lower values of the curves showed a spread of at least a factor of 5. The concentration of active substance which inhibits the activity of EGF-receptor kinase by 50% ($IC_{50}$) was derived from the curves. The compounds according to the invention had $IC_{50}$ values of less than 10 μM.

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, the treatment of nasal polyps, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The compounds of general formula I according to the invention wherein $R^c$ denotes a (2-hydroxyethyl)amino group wherein the carbon skeleton of the (2-hydroxyethyl)-moiety is optionally substituted by one or two $C_{1-3}$-alkyl groups are also suitable for preparing corresponding 2-oxo-morpholin-4-yl derivatives, such as those described in WO 00/55141 or WO 02/18351, for example. For example, the compound of Example 2 may be reacted with methyl bromoacetate to form (S)-4-[(3-chloro-4-fluoro-phenyl) amino]-6-[2-(6-methyl-2-oxo-morpholin-4-yl)ethyloxy]-7-methoxy-quinazoline (cf. Process Example A).

The following Examples are intended to illustrate the invention without restricting it:

Preparation of the Starting Compounds:

EXAMPLE I

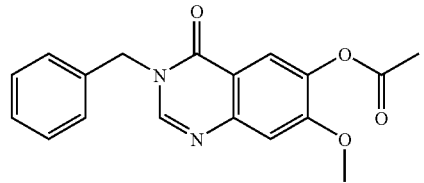

3-benzyl-3,4-dihydro-4-oxo-6-acetyloxy-7-methoxy-quinazoline 169 g of 3,4-dihydro-4-oxo-6-acetyloxy-7-methoxy-quinazoline, 118.8 ml benzyl bromide and 138.2 g potassium carbonate are heated to 35–40° C. in 1600 ml acetone for 8 hours. The mixture is stirred for 15 hours at ambient temperature and then combined with 2000 ml of water. The suspension is cooled to 0° C., the precipitate is suction filtered, washed with 400 ml of water and 400 ml tert.-butylmethylether and dried at 50° C. The solid is dissolved in 4000 ml methylene chloride, filtered and evaporated down. The residue is suspended in tert.-butylmethylether, suction filtered and dried at 50° C. Yield:

203 g (86% of theory)

$R_f$ value: 0.80 (silica gel, methylene chloride/ethanol=9:1)

Mass spectrum (ESI⁺): m/z=325 [M+H]⁺

EXAMPLE II

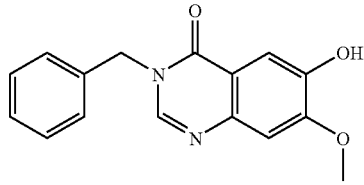

3-Benzyl-3,4-dihydro-4-oxo-6-hydroxy-7-methoxy-quinazoline

Method A:

168.5 g 6-hydroxy-7-methoxy-benzo[d][1,3]oxazin-4-one are dissolved in 1200 ml of toluene and 74.7 ml benzylamine are added. The mixture is refluxed for 15 hours and then cooled to ambient temperature. The precipitate is filtered off and washed with tert.-butylmethylether.

Yield 124 g (72% of theory)

Method B:

200 g 3-benzyl-3,4-dihydro-4-oxo-6-acetyloxy-7-methoxy-quinazoline are suspended in 200 ml of water and 1000 ml of ethanol. 300 ml of 1ON sodium hydroxide solution are added at ambient temperature and the mixture is heated to 30° C. for 1 hour. After the addition of 172 ml acetic acid and 2000 ml of water the mixture is stirred for 20 hours at ambient temperature. The precipitate is suction filtered, washed with water and acetone and dried at 60° C.

Yield: 172.2 g (98% of theory)

$R_f$ value: 0.25 (silica gel, methylene chloride/ethanol= 19:1)

Mass spectrum (ESI$^+$): m/z=283 [M+H]$^+$

EXAMPLE III

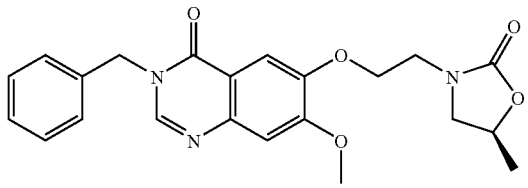

(S)-3-Benzyl-3,4-dihydro-4-oxo-6-[2-(2-oxo-5-methyl-oxazolidin-3-yl)ethyloxy]-7-methoxy-quinazoline Method A 12.34 g (S)-3-benzyl-3,4-dihydro-4-oxo-6-{2-[(2-hydroxypropyl)amino]ethyloxy}-7-methoxy-quinazoline and 8.1 g N,N'-carbonyldiimidazole are suspended in 120 ml of tetrahydrofuran and stirred for 2 hours at ambient temperature. The solvent is removed and the residue is dissolved in 250 ml water. The solution is cooled to 2° C., the precipitate is suction filtered and recrystallised from a mixture of ethyl acetate and diisopropylether and dried at 40° C.

Yield: 11.4 g (87% of theory)

Method B 12.13 g (S)-5-methyl-oxazolidin-2-one are dissolved in 200 ml N-methylpyrrolidone and 13.46 g potassium-tert.-butoxide are added. After 30 minutes 34.48 g of 3-benzyl-3,4-dihydro-4-oxo-6-(2-chloro-ethyloxy)-7-methoxy-quinazoline are added and the mixture is heated to 65° C. for 7.5 hours. After the addition of water the precipitate is suction filtered and washed with water. The solid is purified by column chromatography on silica gel with methylene chloride/ethanol (50:1). The fractions containing product are collected, combined, evaporated down, the residue is recrystallised from ethyl acetate and dried at 40° C.

Yield: 25.5 g (62% of theory)

Method C 2.82 g 3-benzyl-3,4-dihydro-4-oxo-6-hydroxy-7-methoxy-quinazoline, 1.8 g (S)-3-(2-chloro-ethyl)-5-methyl-oxazolidin-2-one and 2.07 g potassium carbonate are heated to 70–75° C. in 30 ml of dimethylformamide for 7.5 hours. The mixture is combined with 90 ml of water and cooled to 0° C. The precipitate is suction filtered, washed with water and dried.

Yield: 2.2 g (53% of theory)

The title compound may also be obtained analogously to Method C using (S)-3-[2-(4-toluenesulphonyloxy)ethyl]-5-methyl-oxazolidin-2-one as alkylating agent.

$R_f$ value: 0.63 (silica gel, methylene chloride/ethanol= 19:1)

Mass spectrum (ESI$^+$): m/z=410 [M+H]$^+$

EXAMPLE IV

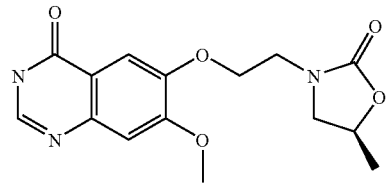

(S)-3,4-dihydro-4-oxo-6-[2-(2-oxo-5-methyl-oxazolidin-3-yl)ethyloxy]-7-methoxy-quinazoline Method A:

27 g (S)-3-benzyl-3,4-dihydro-4-oxo-6-[2-(2-oxo-5-methyl-oxazolidin-3-yl)ethyloxy]-7-methoxy-quinazoline are hydrogenated for 17 hours at a pressure of 50 psi and a temperature of 50° C. with 2 g palladium on activated charcoal (10% Pd) in 200 ml acetic acid. The catalyst is filtered off and the solvent is removed. The residue is recrystallised from ethyl acetate and dried at 50° C.

Yield: 17.5 g (83% of theory)

Method B:

1 g (S)-3,4-dihydro-4-oxo-6-{2-[(2-hydroxypropyl)amino]ethyloxy}-7-methoxy-quinazoline and 0.81 g N,N'-carbonyldiimidazole are refluxed in 20 ml of tetrahydrofuran for 4 hours. The mixture is combined with 40 ml of water and cooled to 0° C. The precipitate is suction filtered, washed with water and dried at 50° C.

Yield: 0.9 g (82% of theory)

$R_f$ value: 0.45 (silica gel, methylene chloride/ethanol=9:1)

Mass spectrum (ESI$^+$): m/z=320 [M+H]$^+$

EXAMPLE V

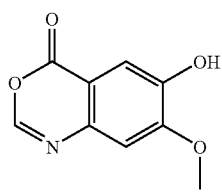

6-Hydroxy-7-methoxy-benzo[d] [1,3]oxazin-4-one 1 g of 2-amino-5-hydroxy-4-methoxy-benzoic acid (prepared by reacting methyl 2-nitro-4,5-dimethoxy-benzoate with potassium hydroxide solution to obtain 2-nitro-5-hydroxy-4-methoxy-benzoic acid-potassium salt and subsequent catalytic hydrogenation in the presence of palladium on activated charcoal) and 20 ml triethyl orthoformate are heated to 100° C. for 2.5 hours. After cooling to ambient temperature the precipitate is suction filtered and washed with diethyl ether.

Yield: 0.97 g (93% of theory)

$R_f$ value: 0.86 (silica gel, methylene chloride/methanol/acetic acid=90:10:1)

Mass spectrum (ESI$^+$): m/z=194 [M+H]$^+$

EXAMPLE VI

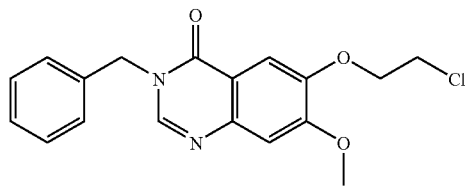

3-Benzyl-3,4-dihydro-4-oxo-6-(2-chloro-ethyloxy)-7-methoxy-quinazoline 98.8 g 3-benzyl-3,4-dihydro-4-oxo-6-hydroxy-7-methoxy-quinazoline, 96.5 g (2-chloro-ethyl) toluene-4-sulphonate and 96.7 g potassium carbonate are heated to 40–45° C. in 500 ml of dimethylformamide for 24 hours. After the addition of 1400 ml of water the precipitate is suction filtered, washed with water and tert.-butylmethylether and dried at 50° C.

Yield: 119 g (98% of theory)

$R_f$ value: 0.45 (silica gel, methylene chloride/ethanol=19:1)

Mass spectrum (ESI$^+$): m/z=345, 347 [M+H]$^+$

EXAMPLE VII

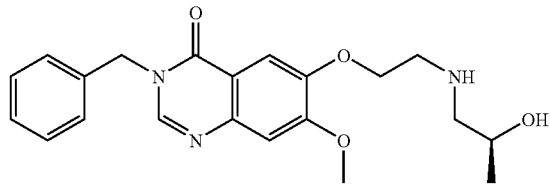

(S)-3-Benzyl-3,4-dihydro-4-oxo-6-{2-[(2-hydroxypropyl)amino]ethyloxy}-7-methoxy-quinazoline 23 g 3-benzyl-3,4-dihydro-4-oxo-6-(2-chloro-ethyloxy)-7-methoxy-quinazoline and 21.1 g sodium carbonate are heated to 135–140° C. in 50 ml N-methylpyrrolidone. 15 g (S)-1-amino-2-propanol dissolved in 100 ml N-methyl-pyrrolidine are added dropwise to this mixture within 25 minutes. The mixture is heated to 135–140° C. for 2 hours, then cooled to ambient temperature and filtered. The solvent is distilled off and the residue is purified by column chromatography on silica gel with methylene chloride/methanol (9:1). The fractions containing product are collected, combined and evaporated down. The residue is dissolved in ethyl acetate and the product is precipitate by the addition of tert.-butyl-methylether. The precipitate is suction filtered and dried.

Yield: 22 g (85% of theory)

$R_f$ value: 0.15 (silica gel, methylene chloride/methanol=9:1)

Mass spectrum (ESI$^+$): m/z=384 [M+H]$^+$

EXAMPLE VIII

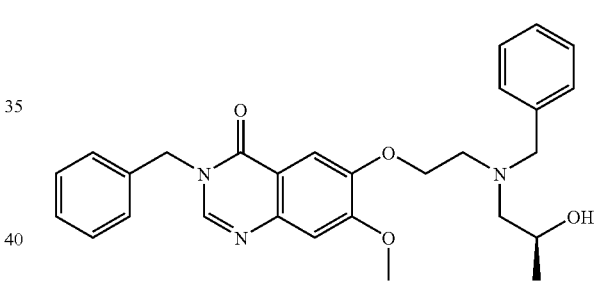

(S)-3-benzyl-3,4-dihydro-4-oxo-6-{2-[N-(2-hydroxypropyl)-N-benzyl-amino]ethyloxy}-7-methoxy-quinazoline 3.45 g 3-benzyl-3,4-dihydro-4-oxo-6-(2-chloro-ethyloxy)-7-methoxy-quinazoline, 1.98 g (S)-1-benzylamino-propan-2-ol, 2.12 g sodium carbonate and 1.45 g sodium iodide are heated to 125° C. in 20 ml N-methylpyrrolidone for 4 hours. After the addition of 70 ml of water, 30 ml diisopropylether and 30 ml of ethyl acetate the precipitate is suction filtered, washed with water and dried at 70° C. The crude product is dissolved in 25 ml of ethyl acetate in the heat, combined with activated charcoal and filtered. The filtrate is combined with 80 ml diisopropylether and cooled to 0° C. The precipitate is suction filtered and dried at 50° C.

Yield: 1.95 g (41% of theory)

$R_f$ value: 0.30 (silica gel, methylene chloride/ethanol=19:1)

Mass spectrum (ESI$^+$): m/z=474 [M+H]$^+$

EXAMPLE IX

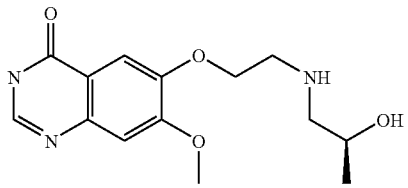

(S)-3,4-dihydro-4-oxo-6-{2-[(2-hydroxypropyl)amino]ethyloxy}-7-methoxy-quinazoline 5.8 g (S)-3-benzyl-3,4-dihydro-4-oxo-6-{2-[N-(2-hydroxypropyl)-N-benzyl-amino]ethyloxy}-7-methoxy-quinazoline are hydrogenated for 8 hours in 50 ml acetic acid at a pressure of 50 psi and 60° C. in the presence of 0.6 g palladium on activated charcoal (10% Pd). The catalyst is filtered off and the solvent is removed. The residue is purified by column chromatography on silica gel with methylene chloride/ethanol/conc. aqueous ammonia=90:10:2. The fractions containing product are collected, combined and evaporated down. The residue is recrystallised from ethanol and dried at 60° C.

Yield: 1.54 g (43% of theory)
$R_f$ value: 0.20 (silica gel, methylene chloride/ethanol/conc. aqueous ammonia=90:10:2)
Mass spectrum (ESI$^+$): m/z=294 [M+H]$^+$

EXAMPLE X

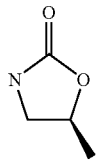

(S)-5-methyl-oxazolidin-2-one

Prepared by reacting (5)-1-amino-2-propanol with diphenyl carbonate in toluene and subsequent fractionated distillation.

Mass spectrum (ESI$^+$): m/z=102 [M+H]$^+$

EXAMPLE XI

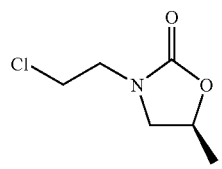

(S)-3-(2-chloro-ethyl)-5-methyl-oxazolidin-2-one 10.11 g (S)-5-methyl-oxazolidin-2-one are dissolved in 150 ml of dimethylformamide. 11.22 g potassium-tert.-butoxide and 22.07 g (2-chloro-ethyl) toluene-4-sulphonate are added and the mixture is heated to 110° C. for 2 hours. The solvent is distilled off and the residue is combined with 150 ml of water. The aqueous phase is extracted twice with 200 ml of ethyl acetate. The organic phase is washed with 100 ml of saturated saline solution. The solvent is removed and the residue is purified by column chromatography over silica gel with methylene chloride/ethanol (50:1). The fractions containing product are collected, combined and evaporated down.

Yield: 6.1 g (37% of theory)
$R_f$ value: 0.40 (silica gel, methylene chloride/ethanol= 49:1)
Mass spectrum (ESI$^+$): m/z=164, 166 [M+H]$^+$

EXAMPLE XII

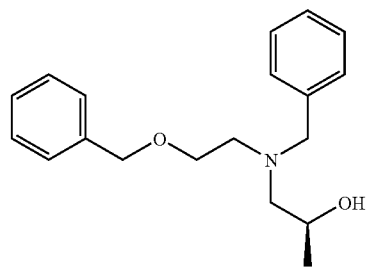

(S)-N-(2-hydroxypropyl)-N-[2-(benzyloxy) ethyl]-benzylamine 10.4 g (S)-1-benzylamino-propan-2-ol, 7.56 ml 2-(benzyloxy)-ethylbromide, 8.71 g potassium carbonate and 100 ml acetonitrile are stirred for 2.5 days at 60° C. A further 0.7 ml 2-(benzyloxy)-ethylbromide and 0.8 g potassium carbonate are added and stirring is continued for another 8 hours at 80° C. The reaction mixture is evaporated down, the residue is distributed between ethyl acetate and water and the organic phase is washed with water and saturated saline solution, dried and evaporated down. 16.8 g of the residue are purified by chromatography through a silica gel column with methylene chloride/methanol.

Yield: 10.4 g (62% of theory)
$R_f$ value: 0.54 (silica gel, methylene chloride/methanol=95:5)
Mass spectrum (ESI$^+$): m/z=300 [M+H]$^+$

EXAMPLE XIII

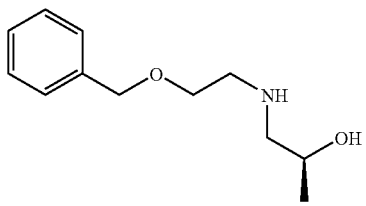

(S)-N-(2-hydroxypropyl)-N-[2-(benzyloxy)ethyl]-amine 5.0 g (S)-N-(2-hydroxypropyl)-N-[2-(benzyloxy)ethyl]-benzylamine are hydrogenated in 50 ml of ethanol for 2 hours at ambient temperature in the presence of 1 g palladium on activated charcoal (10% Pd). The mixture is filtered to remove the catalyst and evaporated to dryness.

Yield: 3.49 g (100% of theory)

R$_f$ value: 0.30 (silica gel, methylene chloride/methanol=9:1)

Mass spectrum (ESI$^+$): m/z=210 [M+H]$^+$

EXAMPLE XIV

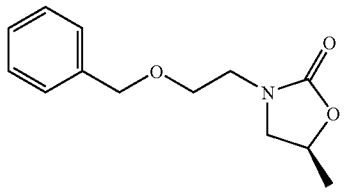

(S)-3-[2-(benzyloxy)ethyl]-5-methyl-oxazolidin-2-one 3.375 g (S)-N-(2-hydroxypropyl)-N-[2-(benzyloxy)ethyl]-amine and 2.615 g N,N'-carbonyldiimidazole are stirred in 35 ml of tetrahydrofuran for 3 hours at ambient temperature. Another 0.523 g N,N'-carbonyldiimidazole are added and the mixture is stirred for a further 2 hours. After the addition of 0.5 ml of water it is stirred for 2.5 days. Then 5 ml of 1M sodium hydroxide solution are added, the mixture is stirred for 1.5 hours, then 3 ml of 1M sodium hydroxide solution are added and the mixture is stirred for another hour. The reaction mixture is evaporated down, and the residue is distributed between ethyl acetate and water. The organic phase is washed with 1M hydrochloric acid, water and saturated saline solution, dried and evaporated to dryness.

Yield: 3.2 g (84% of theory)

R$_f$ value: 0.72 (silica gel, methylene chloride/methanol=95:5)

Mass spectrum (ESI$^+$): m/z=236 [M+H]$^+$

EXAMPLE XV

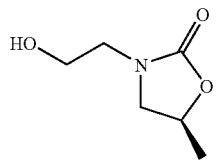

(S)-3-(2-Hydroxyethyl)-5-methyl-oxazolidin-2-one 3.2 g (S)-3-[2-(benzyloxy)ethyl]-5-methyl-oxazolidin-2-one are hydrogenated in 35 ml of ethyl acetate at ambient temperature for 1.5 hours in the presence of 0.7 g palladium on activated charcoal (10% Pd). The catalyst is filtered off and the residue is evaporated to dryness.

Yield: 1.93 g (98% of theory)

R$_f$ value: 0.24 (silica gel, methylene chloride/methanol=95:5)

Mass spectrum (ESI$^+$): m/z=146 [M+H]$^+$

EXAMPLE XVI

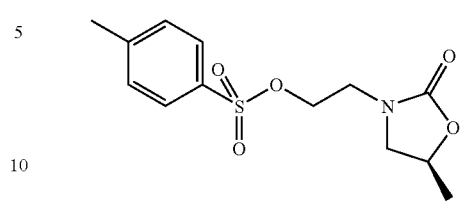

(S)-3-[2-(4-toluenesulphonyloxy)ethyl]-5-methyl-oxazolidin-2-one 2.5 g of 4-toluenesulphonylchloride are added to 1.9 g (S)-3-(2-hydroxyethyl)-5-methyl-oxazolidin-2-one in 5 ml of pyridine while cooling with ice, stirred for 2 hours while cooling with ice and stirred for a further hour at ambient temperature. The reaction mixture is poured onto a mixture of 50 ml ice water and 6 ml concentrated hydrochloric acid, 70 ml of ethyl acetate are added and the mixture is stirred. The organic phase is separated off, washed with water and saturated saline solution, dried and evaporated down.

Yield: 2.8 g (72% of theory)

R$_f$ value: 0.44 (silica gel, ethyl acetate/cyclohexane=7:3)

Mass spectrum (ESI$^+$): m/z=300 [M+H]$^+$

Preparation of the End Compounds:

EXAMPLE 1

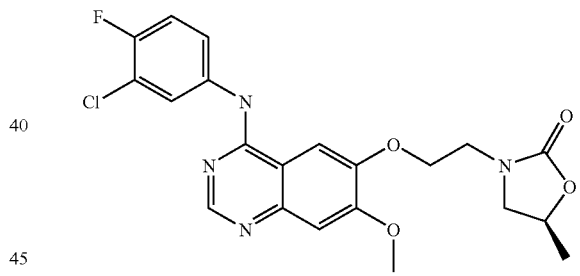

(S)-4-[(3-chloro-4-fluoro-phenyl)amino]-6-[2-(2-oxo-5-methyl-oxazolidin-3-yl)ethyloxy]-7-methoxy-quinazoline 1 g of (S)-3,4-dihydro-4-oxo-6-[2-(2-oxo-5-methyl-oxazolidin-3-yl)ethyloxy]-7-methoxy-quinazoline, 15 ml of thionyl chloride and 0.1 ml of dimethylformamide are refluxed for 2 hours. The solvent is removed and the residue is twice dissolved in 20 ml of toluene and evaporated to dryness. The residue is dissolved in isopropanol and 1 g of 3-chloro-4-fluoro-aniline and 0.82 g of Hünig base are added. The mixture is refluxed for 2 hours. After cooling to 0° C. and adding 30 ml of water the precipitate is suction filtered, washed with 50% aqueous isopropanol and dried at 50° C.

Yield: 0.9 g (64% of theory)

R$_f$ value: 0.27 (silica gel; methylene chloride/ethanol=19:1)

Mass spectrum (ESI$^+$): m/z=447/449 [M+H]$^+$

EXAMPLE 2

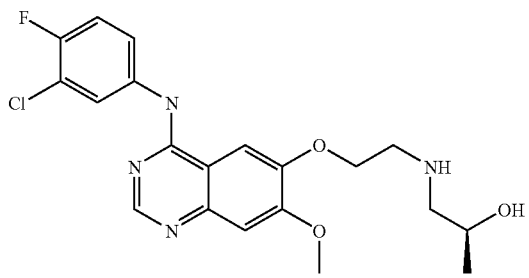

(S)-4-[(3-chloro-4-fluoro-phenyl)amino]-6-{2-[(2-hydroxypropyl)amino]ethyloxy}-7-methoxy-quinazoline 0.8 g of (S)-4-[(3-chloro-4-fluoro-phenyl)amino]-6-[2-(2-oxo-5-methyl-oxazolidin-3-yl)ethyloxy]-7-methoxy-quinazoline and 0.2 g lithium hydroxide are dissolved in a mixture of 20 ml isopropanol and 5 ml of water. The mixture is refluxed for 8 hours, concentrated to 10 ml and cooled to 0° C. After the addition of 10 ml of diisopropylether the precipitate is suction filtered, washed with water and dried at 50° C.

Yield: 0.6 g (79% of theory)

$R_f$ value: 0.38 (silica gel; methylene chloride/methanol/conc. aqueous ammonia=90:10:1)

Mass spectrum (ESI$^+$): m/z=421/423 [M+H]$^+$

EXAMPLE 3

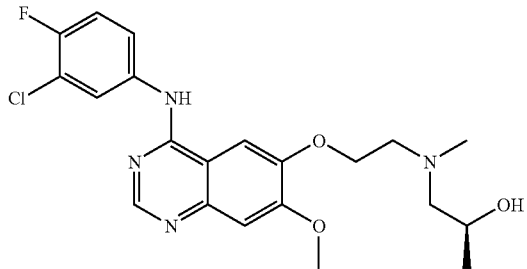

(S)-4-[(3-chloro-4-fluoro-phenyl)amino]-6-{2-[N-(2-hydroxypropyl)-N-methyl-amino]ethyloxy}-7-methoxy-quinazoline A mixture of 210 mg (S)-4-[(3-chloro-4-fluoro-phenyl)amino]-6-{2-[(2-hydroxypropyl)amino]ethyloxy}-7-methoxy-quinazoline, 0.26 ml N-ethyl-diisopropylamine and 4 ml of tetrahydrofuran are stirred for 30 minutes at ambient temperature. Then 94 μl 37% aqueous formalin solution and 318 mg of sodium triacetoxyborohydride are added and the mixture is stirred overnight at ambient temperature. The reaction mixture is combined with 10% potassium carbonate solution and extracted with ethyl acetate. The organic phase is washed with water and saline solution, dried and evaporated down.

Yield: 100 mg (46% of theory)

$R_f$ value: 0.42 (silica gel, methylene chloride/methanol/conc. aqueous ammonia=60:10:1)

Mass spectrum (ESI$^+$): m/z=435, 437 [M+H]$^+$

The following compounds are obtained analogously to Example 3:

(1) (S)-4-[(3-chloro-4-fluoro-phenyl)amino]-6-{2-[N-(2-hydroxypropyl)-N-ethyl-amino]ethyloxy}-7-methoxy-quinazoline

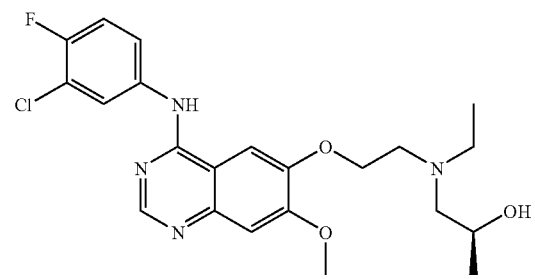

$R_f$ value: 0.60 (silica gel, methylene chloride/methanol/conc. aqueous ammonia=60:10:1)

Mass spectrum (ESI$^+$): m/z=449, 451 [M+H]$^+$ (2) 4-[(3-chloro-4-fluoro-phenyl)amino]-6-{2-[N-(2-hydroxy-2-methyl-propyl)-N-methyl-amino]ethyloxy}-7-methoxy-quinazoline

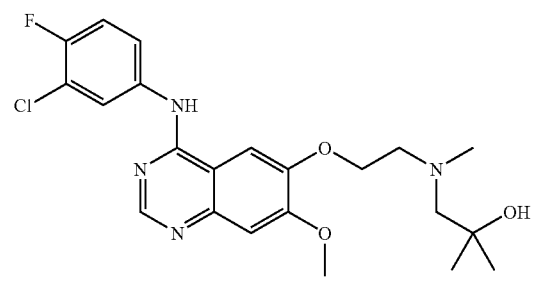

$R_f$ value: 0.40 (silica gel, methylene chloride/methanol/conc. aqueous ammonia=70:10:1)

Mass spectrum (ESI$^+$): m/z=449, 451 [M+H]$^+$ (3) 4-[(3-chloro-4-fluoro-phenyl)amino]-6-{2-[N-(2-hydroxy-2-methyl-propyl)-N-ethyl-amino]ethyloxy}-7-methoxy-quinazoline

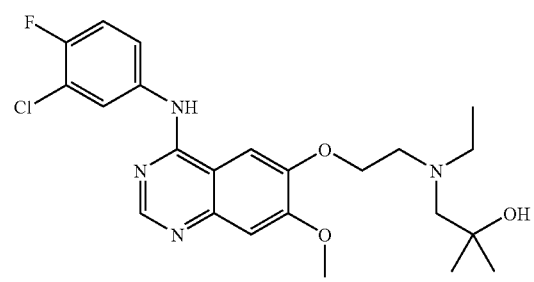

$R_f$ value: 0.44 (silica gel, methylene chloride/methanol/conc. aqueous ammonia=70:10:1)

Mass spectrum (ESI$^+$): m/z=463, 465 [M+H]$^+$

EXAMPLE 4

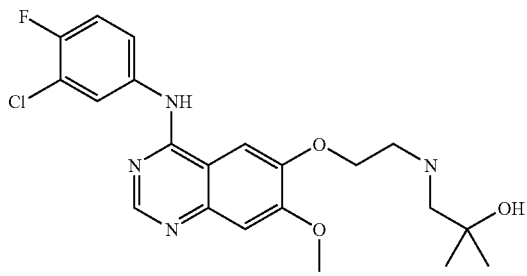

4-[(3-chloro-4-fluoro-phenyl)amino]-6-{2-[(2-hydroxy-2-methyl-propyl)amino]ethyloxy}-7-methoxy-quinazoline A mixture of 4.8 g 4-[(3-chloro-4-fluoro-phenyl)amino]-6-(2-chloroethyloxy)-7-methoxy-quinazoline ($R_f$ value: 0.38, (silica gel, methylene chloride/ethanol=19:1), prepared by reacting 4-[(3-chloro-4-fluoro-phenyl)amino]-6-hydroxy-7-methoxy-quinazoline with (2-chloroethyl)benzenesulphonate in dimethylformamide at 45° C. in the presence of potassium carbonate), 2.23 g of 2-hydroxy-2-methyl-propylamine, 3.33 g sodium carbonate and 25 ml of dimethylformamide are stirred for 3 days at 60° C. The reaction mixture is distributed between ethyl acetate and water, the organic phase is washed with water and saline solution, dried and evaporated down. The residue is purified by chromatography through a silica gel column with methylene chloride/methanol/conc. aqueous ammonia.

Yield: 1.1 g (20% of theory)
$R_f$ value: 0.58 (silica gel, methylene chloride/methanol/conc. aqueous ammonia=60:10:1)
Mass spectrum (ESI$^+$): m/z=435, 437 [M+H]$^+$

EXAMPLE 5

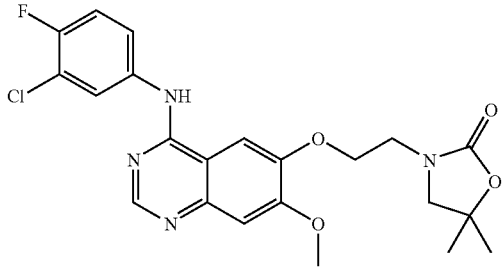

4-[(3-chloro-4-fluoro-phenyl)amino]-6-[2-(2-oxo-5,5-dimethyl-oxazolidin-3-yl)ethyloxy]-7-methoxy-quinazoline 89 mg of N,N'-carbonyldiimidazole are added to 217 mg 4-[(3-chloro-4-fluoro-phenyl)amino]-6-{2-[(2-hydroxy-2-methyl-propyl)amino]ethyloxy}-7-methoxy-quinazoline in 4 ml of tetrahydrofuran and stirred for 18 hours at ambient temperature and for a further 6 hours at 70° C. After the addition of another 40 mg N,N'-carbonyldiimidazole the mixture is again stirred for 3 hours at 70° C. The reaction mixture is cooled in the ice bath, the precipitate is suction filtered, washed with a little tetrahydrofuran and dried.

Yield: 70 mg (30% of theory)
$R_f$ value: 0.50 (silica gel, methylene chloride/methanol/conc. aqueous ammonia=70:10:1)
Mass spectrum (ESI$^+$): m/z=461, 463 [M+H]$^+$ The following compound is obtained analogously to Example 5:

(1) (S)-4-[(3-chloro-4-fluoro-phenyl)amino]-6-[2-(2-oxo-5-methyl-oxazolidin-3-yl)ethyloxy]-7-methoxy-quinazoline

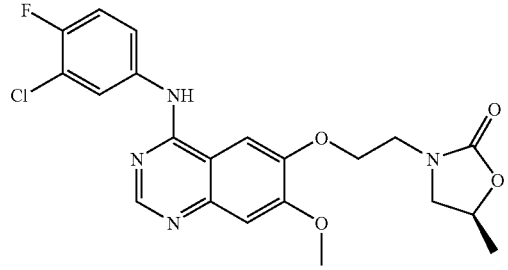

$R_f$ value: 0.65 (silica gel; methylene chloride/ethanol=9:1)
Mass spectrum (ESI$^+$): m/z=447/449 [M+H]$^+$ The following compounds may also be prepared analogously to the foregoing Examples and other methods known from the literature:

| Serial no. | Structure |
|---|---|
| (1) | 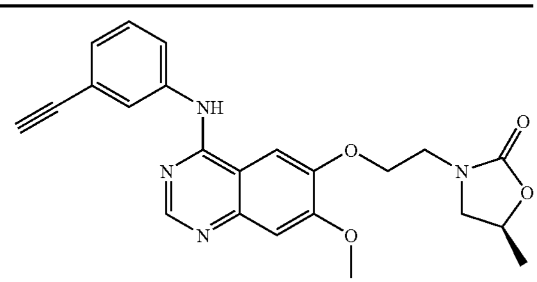 |
| (2) | 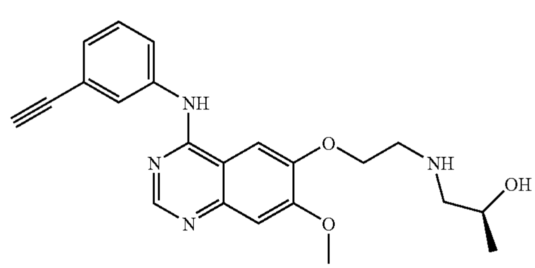 |
| (3) | 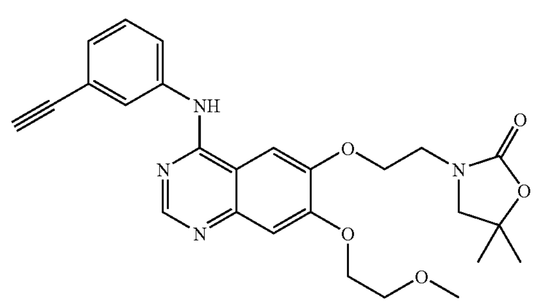 |

| Serial no. | Structure |
|---|---|
| (4) | 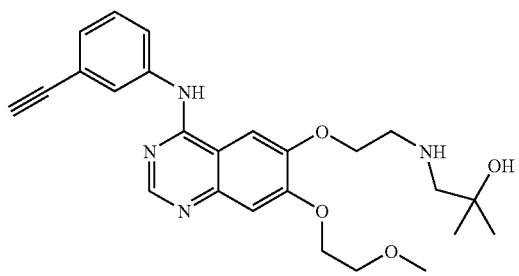 |
| (5) | 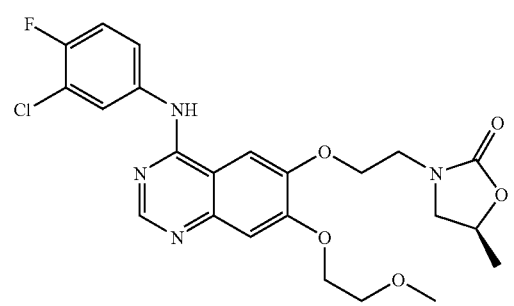 |
| (6) | 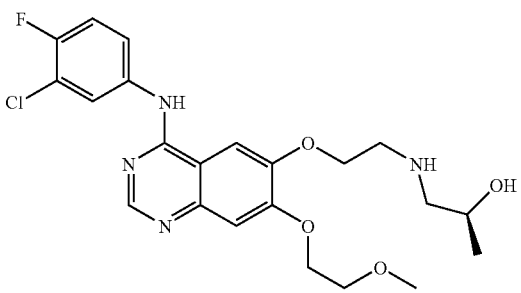 |
| (7) | 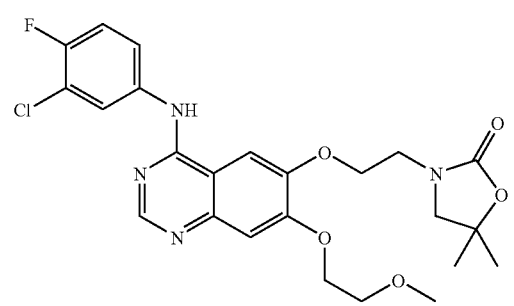 |
| (8) | 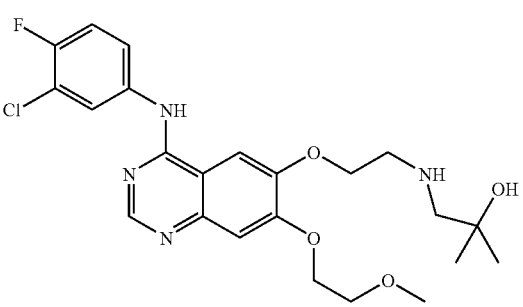 |
| (9) | 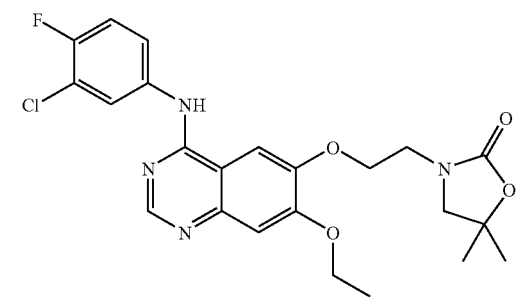 |
| (10) | 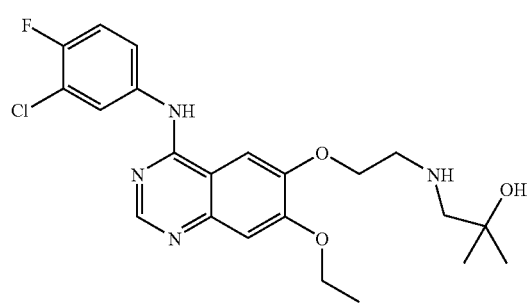 |

EXAMPLE 6

| Coated tablets containing 75 mg of active substance 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| Weight of core: | 230 mg |
|---|---|
| die: | 9 mm, convex |

The tablet cores thus produced are coated with a film consisting essentially of hydroxypropylmethylcellulose. The finished film-coated tablets are polished with beeswax.

Weight of coated tablet: 245 mg.

EXAMPLE 7

Tablets containing 100 mg of active substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

EXAMPLE 8

Tablets containinci 150 mg of active substance
Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

EXAMPLE 9

Hard gelatine capsules containing 150 mg of active substance
1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

EXAMPLE 10

Suppositories containing 150 mg of active substance
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 11

Suspension containing 50 mg of active substance
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 12

Ampoules containing 10 mg active substance

Composition:

| | |
|---|---|
| active substance | 10.0 mg |
| 0.01 N hydrochloric acid q.s. | |
| double-distilled water ad | 2.0 ml |

Preparation:

The active substance is dissolved in the requisite amount of 0.01 N HCl, made isotonic with common salt, filtered sterile and transferred into 2 ml ampoules.

EXAMPLE 13

Ampoules containing 50 mg of active substance

Composition:

| active substance | 50.0 mg |
|---|---|
| 0.01 N hydrochloric acid | q.s. |
| double-distilled water ad | 10.0 ml |

Preparation:

The active substance is dissolved in the necessary amount of 0.01 N HCl, made isotonic with common salt, filtered sterile and transferred into 10 ml ampoules.

EXAMPLE 14

Capsules for powder inhalation containing 5 mg of active substance 1 capsule contains:

| active substance | 5.0 mg |
|---|---|
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule | 3 |

EXAMPLE 15

Solution for inhalation for hand-held nebulisers containing 2.5 mg active substance 1 spray contains:

| active substance | 2.500 mg |
|---|---|
| benzalkonium chloride | 0.001 mg |
| 1N hydrochloric acid | q.s. |
| ethanol/water (50/50) ad | 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulizers (cartridges).

Contents of the container: 4.5 g

PROCESS EXAMPLE A

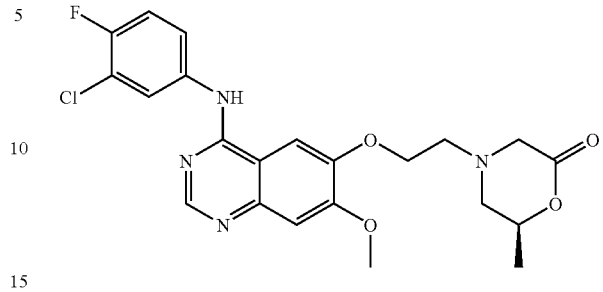

(S)-4-[(3-chloro-4-fluoro-phenyl)amino]-6-[2-(6-methyl-2-oxo-morpholin-4-yl)ethyloxy]-7-methoxy-quinazoline 425 g of (S)-4-[(3-chloro-4-fluoro-phenyl)amino]-6-{2-[(2-hydroxypropyl)amino]ethyloxy}-7-methoxy-quinazoline and 210 ml N-ethyl-diisopropylamine are dissolved in 640 ml N-methylpyrrolidone. After the addition of 105 ml methyl bromoacetate the mixture is stirred for 1 hour at 20–25° C. After the addition of 8500 ml n-butyl acetate and 4300 ml of water the phases are separated and the organic phase is washed with 4300 ml of water. The organic phase is evaporated down at 200 mbar to 50% of the original volume and 4300 ml of n-butyl acetate are added. The mixture is heated to 120–130° C. for 40 hours, filtered and evaporated down to a volume of 2000 ml at 200 mbar. After cooling to −10° C. the precipitate is suction filtered, washed with 800 ml n-butyl acetate and dried at 50° C. The crude product is recrystallised twice from methylethylketone (3750 and 5100 ml).

Yield: 170 g (36% of theory)

Mass spectrum (ESI$^+$): m/z=461/463 [M+H]$^+$.

What is claimed is:

1. A compound of formula

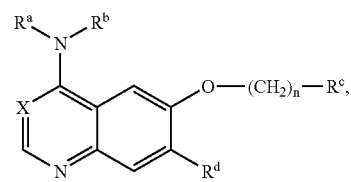

wherein $R^a$ denotes a hydrogen atom or a $C_{1-3}$-alkyl group, $R^b$ denotes a phenyl or 1-phenylethyl group, wherein the phenyl nucleus is substituted in each case by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, a phenyloxy or phenylmethoxy group, while the phenyl moiety of the above-mentioned groups is optionally substituted by a fluorine or chlorine atom, or a pyridyloxy or pyridinylmethoxy group, while the pyridinyl moiety of the above-mentioned groups is optionally substituted by a methyl or trifluoromethyl group, a methyl or methoxy group substituted by 1 to 3 fluorine atoms or a cyano, nitro or amino group, and $R^3$ denotes a hydrogen, fluorine, chlorine or bromine atom or a methyl or trifluoromethyl group, $R^c$ denotes a 2-oxo-oxazolidin-3-yl group optionally substituted by one or two $C_{1-3}$-alkyl groups, $R^d$ denotes a hydrogen atom, a hydroxy group, a $C_{1-3}$-alkyloxy group, a $C_{2-4}$-alkyloxy group which is substituted by a group $R^4$, while $R^4$ denotes a hydroxy, $C_{1-3}$-alkyloxy, $C_{3-6}$-cycloalkyloxy, amino, $C_{1-3}$-alkylamino, di-($C_{1-3}$alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2.2.1]hept-5-yl, 3-oxa-8-aza-bicyclo[3.2.1]oct-8-yl, 8-oxa-3-aza-bicyclo-[3.2.1]oct-3-yl, piperazin-1-yl, 4-$C_{1-3}$-alkyl-piperazin-1-yl, homopiperazin-1-yl or 4-$C_{1-3}$-alkyl-homopiperazin-1-yl group, while the above-mentioned pyrrolidinyl, piperidinyl, piperazinyl- and morpholinyl groups may each be substituted by one or two $C_{1-3}$-alkyl groups, a $C_{3-7}$-cycloalkyloxy or $C_{3-7}$-cycloalkyl-$C_{1-3}$-alkyloxy group, a tetrahydrofuran-3-yloxy, tetrahydropyran-3-yloxy or tetrahydropyran-4-yloxy group, or a tetrahydrofuranyl-$C_{1-3}$-alkyloxy or tetrahydropyranyl-$C_{1-3}$-allyloxy group, X denotes a nitrogen atom and n denotes the number 2, 3 or 4, while, unless otherwise stated, the above-mentioned alkyl groups may be straight-chain or branched, the tautomers, the stereoisomers, the mixtures thereof and the salts thereof.

2. A compound according to claim 1, wherein $R^a$ denotes a hydrogen atom, $R^b$ denotes a 3-bromophenyl, 3,4-difluorophenyl, 3-chloro-4-fluoro-phenyl or a 3-ethynylphenyl group, $R^c$ denotes a a 2-oxo-5-methyl-oxazolidin-3-yl, 2-oxo-5-ethyl-oxazolidin-3-yl, 2-oxo-5,5-dimethyl-oxazolidin-3-yl or 2-oxo-5,5-diethyl-oxazolidin-3-yl group, $R^d$ denotes a hydrogen atom, a methoxy, ethyloxy or 2-methoxyethyloxy group, a cyclobutyloxy, cyclopentyloxy or cyclohexyloxy group, a cyclopropylmethoxy, cyclobutylmethoxy, cyclopentylmethoxy or cyclohexylmethoxy group, a tetrahydrofuran-3-yloxy, tetrahydropyran-3-yloxy or tetrahydropyran-4-yloxy group, or a tetrahydrofuranylmethoxy or tetrahydropyranylmethoxy group, X denotes a nitrogen atom, and n denotes the number 2 or 3, the tautomers, the stereoisomers, the mixtures thereof and the salts thereof.

3. A compound according to claim 1, wherein $R^a$ denotes a hydrogen atom, $R^b$ denotes a 3-chloro-4-fluoro-phenyl group or 3-ethynylphenyl group, $R^c$ denotes a 2-oxo-5-methyl-oxazolidin-3-yl or 2-oxo-5,5-dimethyl-oxazolidin-3-yl group, $R^d$ denotes a methoxy, ethyloxy or 2-methoxyethyloxy group, X denotes a nitrogen atom, and n denotes the number 2, the tautomers, the stereoisomers, the mixtures thereof and the salts thereof.

4. A compound according to claim 1 selected from the group consisting of:

a) (S)-4[(3-chloro-4-fluoro-phenyl)amino]-6-[2-(2-oxo-5-methyl-oxazolidin-3-yl)ethyloxy]-7-methoxy-quinazoline (b) 4-[(3-chloro-4-fluoro-phenyl)amino]-6-[2-(2-oxo-5,5-dimethyl-oxazolidin-3-yl)ethyloxy]-7-methoxy-quinazoline, and the salts thereof.

5. Physiologically acceptable salts of the compounds according to claim 1 with inorganic or organic acids.

6. Pharmaceutical compositions containing a compound according to claim 1 or a physiologically acceptable salt thereof optionally together with one or more inert carriers and/or diluents.

* * * * *